US006806292B2

(12) United States Patent
Riebel et al.

(10) Patent No.: US 6,806,292 B2
(45) Date of Patent: Oct. 19, 2004

(54) SUBSTITUTED IMIDE DERIVATIVES

(75) Inventors: Hans-Jochem Riebel, Selters (DE); Stefan Herrmann, Langenfeld (DE); Achim Hense, Leichlingen (DE); Ernst-Rudolf Gesing, Erkrath (DE); Kristian Kather, Köln (DE); Stefan Lehr, Langenfeld (DE); Wolfram Andersch, Gladbach (DE); Mark Wilhelm Drewes, Langenfeld (DE); Dieter Feucht, Monheim (DE); Achim Harder, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/182,286
(22) PCT Filed: Jan. 18, 2001
(86) PCT No.: PCT/EP01/00530
§ 371 (c)(1),
(2), (4) Date: Jul. 26, 2002
(87) PCT Pub. No.: WO01/56975
PCT Pub. Date:Aug. 9, 2001

(65) Prior Publication Data
US 2003/0100613 A1 May 29, 2003

(30) Foreign Application Priority Data
Jan. 31, 2000 (DE) .......................................... 100 04 084

(51) Int. Cl.$^7$ ........................ A01N 47/40; C07C 249/02; C07C 255/61; C07C 243/02; C07C 251/02
(52) U.S. Cl. ........................ 514/609; 504/343; 514/610; 564/103; 564/104; 564/108
(58) Field of Search ................................ 564/103, 104, 564/108; 504/343; 514/609, 610

(56) References Cited

U.S. PATENT DOCUMENTS

| 3,910,938 | A | * | 10/1975 | Ikekawa et al. | ......... | 260/295 A |
| 4,491,595 | A | | 1/1985 | Niemers et al. | ............ | 424/326 |
| 5,185,351 | A | * | 2/1993 | Finkelstein et al. | ......... | 514/397 |
| 5,304,566 | A | * | 4/1994 | Ishimitsu et al. | ........... | 514/357 |
| 5,418,250 | A | * | 5/1995 | Finkelstein et al. | ......... | 514/397 |
| 5,612,358 | A | * | 3/1997 | Ishimitsu et al. | ........... | 514/357 |
| 6,638,979 | B1 | * | 10/2003 | Riebel et al. | ............... | 514/609 |

FOREIGN PATENT DOCUMENTS

| DE | 199 24 273 | * | 1/2000 |
| EP | 04 18 199 | * | 3/1991 |
| JP | 10-7648 | * | 1/1998 |
| WO | 93/04032 | * | 3/1993 |
| WO | 94/29268 | * | 12/1994 |

OTHER PUBLICATIONS

J. Org. Chem. USSR (English), vol. 9, (month unavailable) 1973, pp. 1233–1236, "Reactions Of Carboxylic Acid Hydrazides with 2–Methyl–1–Nitroisothiorea" by Zh. N. Fidler et al.*

Bull. Soc. Chim. Belg., vol. 90/n°, Jan. 1981, pp. 89–98, "Synthesis of Symmetrical 1,6–Dihetero–6a$\lambda^4$–Thia–3, 4–Diaza–Pentalenes From 5–Amino–1,2,3,4–Thiatriazole" by G. L'abbe and Guido Vermeulen.*

Journal of Organometallic Chemistry, 97, (month unavailable) 1975, pp. 39–44, "Reactions Of Thioamides With Bis(Tripphenylstannyl)–Carbodiimide and (Triphenylstannyl)Cyanamide" by E. J. Kupchik and H. E. Hanke.*

Tetrahedron Letters, No. 53, pp. 5523–5526, (month unavailable) 1968, "Thioacylierung Von Cyanamid" by Klaus Hartke und Bernd Seib.

Synthesis, (month unavailable) 1975, pp. 332–334, "A Convenient Synthesis of Aryl Dicyandiamides from N–Cyano–S–methylisothiourea" by R. W. Turner.

J. Org. Chem., 35, (month unavailable) 1970, pp. 2068–2069, "Elimination of Methyl Mercaptan from N–Substituted N'–Cyano–S–methylisothioureas. Evidence for N–Cyanocarbodiimides" by C. Gordon McCarty et al.

JACS, 76, Apr. 5, 1954, pp. 1877–1879, "The Preparation and Reactions of 2–Alkyl–1 (or 3)–nitro–2–thiopseudourea. Part I. Reaction with Amines" by L. Fishbein and J. A. Gallaghan.

(List continued on next page.)

Primary Examiner—Peter O'Sullivan
(74) Attorney, Agent, or Firm—Richard E. L. Henderson; Raymond J. Harmuth

(57) ABSTRACT

The present invention relates to novel substituted imide derivatives of the general formula (I)

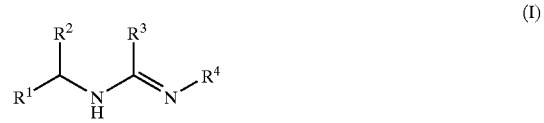

(I)

in which $R^1$ represents optionally substituted cycloalkyl, $R^2$ represents optionally substituted alkyl or optionally substituted cycloalkyl, $R^3$ represents alkyl, alkoxy, alkylthio, amino, alkylamino or dialkylamino and $R^4$ represents cyano or nitro, and to processes for their preparation and to their use for controlling animal pests and as herbicides.

9 Claims, No Drawings

OTHER PUBLICATIONS

Chem. Ber. 100, pp. 2604–2615, (month unavailable) 1967, "Über den N–Cyan–imidokohlensäure–diäthylester und O–Äthyl–N–cyan–isoharstoffe" by E. Allenstein und R. Fuchs.

Recueil dis travaux, Chemiques des Pays–Bas, 81, (month unavailable) 1962, pp. 69–72, "Note On The Conversion Of The Amino Group Of Amino Acids Into The Nitroguanidino Group" by N. Heyboer et al.

J. Org. Chem., 28, Jul. 1963, pp. 1816–1821, "N–Cyanoimidates" by K. R. Huffman and F. C. Schaefer.

Chem. Ind., XXXVII, Oktober 1985, pp. 730–732, "Schiffsfarben—eine Spezialität der seenahen Lackindustrie" by H. R. Ungerer.

* cited by examiner

SUBSTITUTED IMIDE DERIVATIVES

The present application relates to novel substituted imide derivatives, to a process for their preparation and to their use for controlling animal pests and as herbicides.

Certain imide derivatives are already known (cf. WO 91/04 965, WO 93/04 032, EP-A-403 159; J. Organomet. Chem. (1975), 97 (1), pp. 39–44; Bul. Soc. Chim. Belg. (1981), 90 (1), pp. 89–98). Insecticidal and/or herbicidal properties of some of these compounds have also been disclosed.

This invention, accordingly, provides novel substituted imide derivatives of the general formula (I)

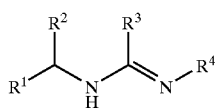
(I)

in which
 $R^1$ represents optionally substituted cycloalkyl,
 $R^2$ represents optionally substituted alkyl or optionally substituted cycloalkyl,
 $R^3$ represents alkyl, alkoxy, alkylthio, amino, alkylamino or dialkylamino and
 $R^4$ represents cyano or nitro.

If appropriate, the imide derivatives of the formula (I) can also be present as optical and/or geometrical isomers. The present invention relates both to the various isomer mixtures and to the pure isomers.

The novel substituted imide derivatives of the formula (I) are obtained when amines of the formula (II)

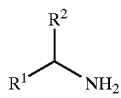
(II)

in which
 $R^1$ and $R^2$ are as defined above are reacted with ethane-imidate of the formula (III)

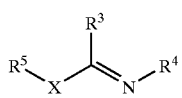
(III)

in which
 $R^3$ and $R^4$ are as defined above,
 $R^5$ represents alkyl and X represents oxygen or sulphur in the presence of a diluent.

The novel imideamide derivatives of the general formula (I) have highly pronounced biological properties and are particularly suitable for controlling animal pests, such as insects, arachnids and in particular nematodes, encountered in agriculture, in forests, in the protection of stored products and materials and in the hygiene sector; for controlling animal pests, such as parasitic nematodes, in veterinary medicine; and also for use as herbicides.

The formula (I) provides a general definition of the compounds according to the invention. Preferred substituents or ranges of the radicals listed in the formulae above and below are illustrated below.

$R^1$ preferably represents $C_3$–$C_6$-cycloalkyl which is optionally mono- to trisubstituted by identical or different substituents from the group consisting of halogen, $C_1$–$C_4$-alkyl, $C_1$–$C_4$-alkoxy and $C_1$–$C_4$-alkylthio.

$R^2$ preferably represents $C_1$–$C_4$-alkyl which is optionally substituted by halogen, cyano or $C_1$–$C_4$-alkoxy or represents $C_3$–$C_6$-cycloalkyl which is optionally mono- to trisubstituted by identical or different substituents from the group consisting of halogen, $C_1$–$C_4$-alkyl, $C_1$–$C_4$-alkoxy and $C_1$–$C_4$-alkylthio.

$R^3$ preferably represents $C_1$–$C_4$-alkyl, $C_1$–$C_4$-alkoxy, $C_1$–$C_4$-alkylthio, amino, $C_1$–$C_4$-alkylamino or di-($C_1$–$C_4$)-alkylamino.

$R^1$ particularly preferably represents cyclopentyl or cyclohexyl, each of which is optionally mono- to trisubstituted by identical or different substituents from the group consisting of fluorine, chlorine, bromine, methyl, ethyl, methoxy, ethoxy, methylthio and ethylthio.

$R^2$ particularly preferably represents methyl, ethyl or n- or i-propyl, each of which is optionally substituted by cyano, fluorine, chlorine, methoxy or ethoxy; or represents cyclopentyl or cyclohexyl, each of which is optionally mono- to trisubstituted by identical or different substituents from the group consisting of fluorine, chlorine, bromine, methyl, ethyl, methoxy, ethoxy, methylthio and ethylthio.

$R^3$ particularly preferably represents methyl, ethyl, n- or i-propyl; n-, i-, s- or t-butyl; methoxy, ethoxy, n- or i-propoxy; methylthio, ethylthio, n- or i-propylthio; amino; methylamino, ethylamino, n- or i-propylamino; ethylmethyl-amino, dimethylamino, diethyl amino, methyl-n-propyl -amino, methyl-i-propylamino, ethyl-n-propyl-amino, ethyl-i-propyl-amino, i-propyl-n-propyl-amino or diisopropylamino.

$R^1$ very particularly preferably represents cyclopentyl or cyclohexyl, each of which is optionally mono- or disubstituted by identical or different substituents from the group consisting of chlorine, methyl and methoxy.

$R^2$ very particularly preferably represents methyl, ethyl or isopropyl.

$R^3$ very particularly preferably represents methyl, ethyl, isopropyl; methoxy, ethoxy, isopropoxy; methylthio, ethylthio, isopropylthio; amino; methylamino, ethylamino; dimethylamino, ethylmethylamino or diethylamino.

In the definitions, the hydrocarbon chains, such as, for example, alkyl, are in each case straight-chain or branched.

Preference according to the invention is given to those compounds of the formula (I) which contain a combination of the meanings listed above as being preferred.

Particular preference according to the invention is given to those compounds of the formula (I) which contain a combination of the meanings listed above as being particularly preferred.

Very particular preference according to the invention is given to those compounds of the formula (I) which contain a combination of the meanings listed above as being very particularly preferred.

Using, for example, R-(–)-cyclohexylamine and methylthio N-cyano-ethaneimidate as starting materials, the course of the reaction of the process according to the invention can be represented by the following equation:

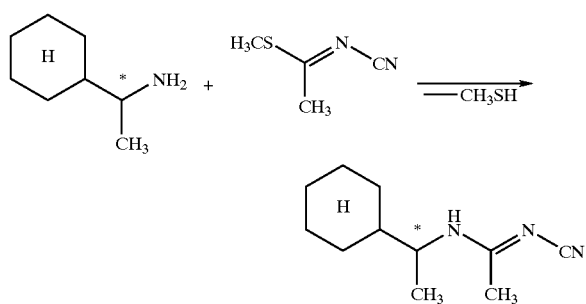

The amines of the formula (II) required as starting materials for carrying out the process according to the invention are generally known compounds of organic chemistry and/or obtainable in a generally known manner. The cyclohexylamine derivatives of the formula (II) can be obtained particularly advantageously by hydrogenation of the corresponding phenylamine derivatives.

The formula (III) provides a general definition of the ethaneimidates further to be used as starting materials in the process according to the invention. In this formula, $R^5$ preferably represents $C_1$–$C_4$-alkyl, such as, in particular, methyl or ethyl.

Most of the N-cyano-ethaneimidates are known (cf., for example, J. Org. Chem. 28, 1816 (1963); Chem. Berichte 100, 2604 (1967); Tetrahedron Letters 1968, 5523; Synthesis 1975, 332; J. Org. Chem. 35, 2067 (1970); U.S. Pat. No. 3,910,928) and/or they can be obtained by customary processes.

Some of the N-nitro-ethaneimidates are also known (cf., for example, J. Org. Chem. USSR (English) 9 (1973), 1233–1236; JACS 76 (1954), 1877; Rec. Trav. Chim. Pay-Bas 81, 69 (1962); JP-A-0156947), and/or they can be obtained by customary processes, such as, in particular, by customary nitration of the corresponding $NO_2$-free ethaneimidates of the formula (III).

The process according to the invention is preferably carried out in the presence of a diluent. Preference is given to using alcohols, such as methanol and ethanol; nitrites, such as acetonitrile, or esters, such as ethyl acetate. It is also possible to carry out the process in water or organic/aqueous mixtures.

When carrying out the process according to the invention, preference is given to using equimolar amounts; however, it is also possible to employ an excess of one or the other starting material.

When carrying out the process according to the invention, the reaction temperatures can be varied within a relatively wide range. In general, the process is carried out at temperatures between 0° C. and 100° C., preferably between 20° C. and 80° C.

Work-up and isolation of the end products are carried out in a generally known manner.

The active compounds are suitable for controlling animal pests, in particular insects, arachnids and nematodes, which are encountered in agriculture, in forests, in the protection of stored products and of materials, and in the hygiene sector, and have good plant tolerance and favourable toxicity to warm-blooded animals. The active compounds are particularly suitable for controlling nematodes. They may be preferably employed as crop protection agents. They are active against normally sensitive and resistant species and against all or some stages of development. The abovementioned pests include:

From the order of the Isopoda, for example, *Oniscus asellus, Armadillidium vulgare* and *Porcellho scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectulanrus, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus*, *Ptinus* spp., *Niptus hololeucus*, *Gibbium psylloides*, *Tribolium* spp., *Tenebrio molitor*, *Agriotes* spp., *Conoderus* spp., *Melolontha melolontha*, *Amphimallon solstitialis*, *Costelytra zealandica* and *Lissorhoptrus oryzophilus*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster*, *Musca* spp., *Fannia* spp., *Calliphora erythrocephala*, *Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus*, *Oscinella frit*, *Phorbia* spp., *Pegomyia hyoscyami*, *Ceratitis capitata*, *Dacus oleae*, *Tipula paludosa*, *Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus*, *Latrodectus mactans*, *Acarus siro*, *Argas* spp., *Ornithodoros* spp., *Dermanyssus gallinae*, *Eriophyes ribis*, *Phyllocoptruta oleivora*, *Boophilus* spp., *Rhipicephalus* spp., *Amblyomma* spp., *Hyalomrma* spp., *Ixodes* spp., *Psoroptes* spp., *Chorioptes* spp., *Sarcoptes* spp., *Tarsonemus* spp., *Bryobia praetiosa*, *Panonychus* spp., *Tetranychus* spp., *Hemitarsonemus* spp., and *Brevipalpus* spp.

The phytoparasitic nematodes include, for example, *Pratylenchus* spp., *Radopholus similis*, *Ditylenchus dipsaci*, *Tylenchulus semipenetrans*, *Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

In particular, the compounds of the formula (I) according to the invention have good nematicidal activity. Thus, they can be used with particularly good results, for example, for controlling *Meloidogyne incognita*.

The active compounds according to the invention can be used as defoliants, desiccants, haulm killers and, especially, as weed killers. Weeds in the broadest sense is understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledonous crops of the izenera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and squares with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention have strong herbicidal activity and a broad spectrum of activity when applied on the soil and to above-ground parts of plants. To a certain extent, they are also suitable for the selective control of monocotyledonous and dicotyledonous weeds in monocotyledonous and dicotyledonous crops, both by the pre-emergence and by the post-emergence method.

If appropriate, the compounds according to the invention can, at certain concentrations and application rates, also be employed as microbicides, for example as fungicides, antimycotics and bactericides. If appropriate, they can also be used as intermediates or precursors in the synthesis of other active compounds.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compounds can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is liquid solvents, and/or solid carriers, optionally with the use of surfactants, that is emulsifiers and/or dispersants, and/or foam-formers.

If the extender used is water, it is also possible to employ, for example, organic solvents as auxiliary solvents. Essentially, suitable liquid solvents are: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, nethyl isobutyl ketone or cyclohexanone, strongly polar solvents, such as dimethylformamide and dimethyl sulphoxide, and also water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers, such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants, such as inorganic pigments, for example iron oxide, titanium oxide and Prussian Blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95% by weight of active compound, preferably between 0.5 and 90%.

The active compound according to the invention can be present in commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable examples of co-components in mixtures are the following compounds:

Fungicides aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imnibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyidithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlatmide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyirmino)-N-methyl-2-phenoxy-phenylacetamide,
1-isopropyl {2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidindione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinol,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]4-methoxy-1H-pyrrolo[2,3-d]pyrinidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pynidine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetanide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinarnine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-((6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphorarnidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides abamectin, acephate, acetamiprid, acrinathrin, alanycarb, aldicarb, aldoxycarb, alphacypermethrin, alphamethrin, arnitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cyclopren, cycloprothrin, cyfluthrin, cyhalothrin, cyhexatin, cypennethrin, cyromazine,
deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M,

*Paecilomyces fumosoroseus,* parathion A, parathion M, pernethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, theta-cypennethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii,*

YI5302, zeta-cypermethrin, zolaprofos, (1R-cis)-[5-(phenylmethyl)-3-furanyl]-methyl-3-[(dihydro-2-oxo-3(2H)-furanylidene)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl) phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone, Bacillus thuringiensis strain EG-2348, 2-benzoyl-1-(1,1-dimethylethyl)-hydrazinobenzoic acid, 2,2-dimethyl-3-(2,4-dichlorophenyl)-2-oxo-1-oxaspiro[4.5] dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl -2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, BAS-662H, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafen-strole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxy-sulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

When used as herbicides, the active compounds can be applied as such, in the form of their formulations or of the use forms prepared therefrom by further dilution, such as ready-to-use solutions, suspensions, emulsions, powders, pastes and granules. Application is carried out in a customary manner, for example by watering, spraying, atomizing, broadcasting.

The active compounds according to the invention can be applied before or after emergence of the plants. They can also be incorporated into the soil prior to sowing.

The application rate used can vary within a relatively wide range. Essentially, it depends on the kind of effect desired. In general, the application rates are between 1 g and 10 kg of active compound per hectare of soil surface, preferably between 5 g and 5 kg per ha.

Having low toxicity to warm-blooded animals, the active compounds of the formula (I) are also suitable for controlling pathogenic endoparasites and ectoparasites which occur in humans and in animal keeping and animal breeding, in productive animals, breeding animals, zoo animals, laboratory animals, animals for experimentation and pets. They are active against all or individual stages of development of the pests and again resistant and normally sensitive species. By controlling the pathogenic parasites it is intended to reduce disease, mortality and reductions in yield (for example in the production of meat, milk, wool, hides, eggs, honey, etc.), so that the use of the active compounds enables more economical and simpler animal keeping. The pathogenic endoparasites include cestodes, trematodes, nematodes; the ectoparasites include arthropods, preferably insects and arachnids.

The following endoparasites may be mentioned in particular:

From the order of the Pseudophyllidea, for example: *Diphyllobothrium* spp., *Spirometra* spp., *Schistocephalus* spp., *Ligula* spp., *Bothridium* spp., *Diphlogonoporus* spp.

From the order of the Cyclophyllidea, for example: *Mesocestoides* spp., *Anoplocephala* spp., *Paranoplocephala* spp., *Moniezia* spp., *Thysanosomsa* spp., *Thysaniezia* spp., *Avitellina* spp., *Stilesia* spp., *Cittotaenia* spp., *Anhyra* spp., *Bertiella* spp., *Taenia* spp., *Echinococcus* spp., *Hydratigera* spp., *Davainea* spp., *Raillietina* spp., *Hymenolepsis* spp., *Echinolepsis* spp., *Echinocotyle* spp., *Diorchis* spp., *Dipylidium* spp., *Joyeuxiella* spp., *Diplopylidium* spp.

From the sub-class of the Monogenea, for example: *Cyrodactylus* spp., *Dactylogyrus* spp., *Polystoma* spp.

From the sub-class of the Digenea, for example: *Diplostomum* spp., *Posthodiplostomum* spp., *Schistosoma* spp., *Trichobilharzia* spp., *Omithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhloccelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonismus* spp., *Dicrocoelium* spp., *Collyriclum* spp., *Nanophyetus* spp., *Opisthorchis* spp., *Clonorchis* spp., *Metorchis* spp., *Heterophyes* spp., *Metagonimus* spp.

From the order of the Enoplida, for example: *Trichuris* spp., *Capillaria* spp., *Trichlomosoides* spp., *Trichinella* spp.

From the order of the Rhabditia, for example: *Micronema* spp., *Strongyloides* spp.

From the order of the Strongylida, for example: *Stronylus* spp., *Triodontophorus* spp., *Oesophagodontus* spp., *Trichonema* spp., *Gyalocephalus* spp., *Cylindropharynx* spp., *Poteriostromum* spp., *Cyclococercus* spp., *Cylicostephanus* spp., *Oesophagostomum* spp., *Chabertia* spp., *Stephanurus* spp., *Acylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongyius* spp., *Spicocaulus* spp., *Elaphostrongylus* spp., *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Oxyurida, for example: *Oxyuris* spp., *Enterobius* spp., *Passalurus* spp., *Syphacia* spp., *Aspiculuris* spp., *Heterakis* spp.

From the order of the Ascaridia, for example: *Ascaris* spp., *Toxascaris* spp., *Toxocara* spp., *Parascaris* spp., *Anisakis* spp., *Ascaridia* spp.

From the order of the Spirurida, for example: *Gnathostoma* spp., *Physaloptera* spp., *Thelazia* spp., *Gongylonema* spp., *Habronema* spp., *Parabronema* spp., *Draschia* spp., *Dracunculus* spp.

From the order of the Filariida, for example: *Stephanofilaria* spp., *Parafilaria* spp., *Setaria* spp., *Loa* spp., *dirofilaria* spp., *Litomosoides* spp., *Brugia* spp., *Wuchereria* spp., *Onchocerca* spp.

From the group of the Gigantohynchida, for example: *Filicollis* spp., *Moniliformis* spp., *Macracanthorhynchus* spp., *Prosthenorchis* spp.

The ectoparasites include, in particular:

From the order of the Anoplura, for example, *Haematopinus* spp., *Linognathus* spp., *Solenopotes* spp., *Pediculus* spp., *Pthirus* spp.;

From the order of the Mallophaga, for example, *Trimenopon* spp., *Menopon* spp., *Eomenacanthus* spp., *Menacanthus* spp., *Trichodectes* spp., *Felicola* spp., *Damalinea* spp., *Bobiola* spp.;

From the order of the Diptera, for example, *Chrysops* spp., *Tabanus* spp., *Musca* spp., *Hydrotaea* spp., *Muscina* spp., *Haematobosca* spp., *Haematobia* spp., *Stomoxys* spp., *Fannia* spp., *Glossina* spp., *Lucilia* spp., *Calliphora* spp., *Auchmeromyia* spp., *Cardylobia* spp., *Cochiomyia* spp., *Chrysomyia* spp., *Sarcophaga* spp., *Wohlfartia* spp., *Gaserophilus* spp., *Oesteromyia* spp., *Oedemagena* spp., *Hyporma* spp., *Oestrus* spp., *Rhinoestrus* spp., *Melophagus* spp., *Hippobosca* spp.

From the order of the Siphonaptera, for example, *Ctenocephalides* spp., *Echidnophaga* spp., *Ceratophyllus* spp.

From the order of the Metastigmata, for example, *Hyalomma* spp., *Rhipicephalus* spp., *Boophilus* spp., *Amblyomma* spp., *Haemophysalis* spp., *Dermacentor* spp., *Ixodes* spp., *Argas* spp., *Ornithodorus* spp., *Otobius* spp.;

From the order of the Mesastigmata, for example, *Dermanyssus* spp., *Ornithonyssus* spp., *Pneumonyssus* spp.

From the order of the Prostigmata, for example, *Cheyletiella* spp., *Psorergates* spp., *Myobia* spp., *Demdex* spp., *Neotrombicula* spp.;

From the order of the Astigmata, for example, *Acarus* spp., *Myocoptes* spp., *Psoroptes* spp., *Chorioptes* spp., *Otodectes* spp., *Sarcoptes* spp., *Notoedres* spp., *Knemidocoptes* spp., *Neoknemidodoptex* spp., *Lytodites* spp., *Laminosioptes* spp.

The productive and breeding animals include mammals, such as, for example, cattle, horses, sheep, pigs, goats, camels, water buffalo, donkeys, rabbits, fallow deer and reindeer, fur-bearing animals, such as, for example, mink, chinchilla and raccoon, birds, such as, for example, hens, geese, turkeys and ducks, fresh- and salt-water fish, such as, for example, trout, carp and eels, reptiles, insects, such as, for example, honey-bee and silkworm.

Laboratory and experimental animals include, for example, mice, rats, guinea-pigs, golden hamsters, dogs and cats.

The pets include, for example, dogs and cats.

Administration can be effected prophylactically as well as therapeutically.

The active compounds are administered, either directly or in the form of suitable preparations, enterally, parenterally, dermally, nasally, by treating the habitat or with the aid of shaped articles containing the active comopund, such as, for example, strips, plates, tapes, collars, ear tags, limb bands or marking devices.

Enteral administration of the active compounds is effected, for example, orally in the form of powders, tablets, capsules, pastes, boluses, drenches, granules, of solutions, suspensions or emulsions which can be applied orally, of medicated feed or drinking water. Dermal application is effected, for example, in the form of dipping, spryaing or pouring-on and spotting-on and powdering-on. Parenteral administration is effected, for example, in the form of injection (intramuscularly, subcutaneously, intravenously or intraperitoneally) or by implants.

Particular emphasis is given to the preparations for dermal application. These include solutions, suspension concentrates and emulsion concentrates and microemulsions which are diluted with water prior to use, pour-on and spot-on formulations, powders and dusts, aerosols and shaped articles containing the active compound, and also dust-bags and back-rubbers.

These preparations are produced in a known manner, for example by mixing the active compound with extenders, i.e. liquid solvents, if appropriate using surfactants, i.e. emulsifiers and/or dispersants. If the extender used is water, it is also possible to use, for example, organic solvents as auxiliary solvents.

In addition to water, the liquid diluents include alcohols, such as methanol, ethanol, isopropanol, n-butanol, amyl alcohol, octanol;

glycols, such as propylene glycol, 1,3-butylene glycol, ethyl glycol, dipropylene glycol monomethyl ether;

glycerol;

aromatic alcohols, such as benzyl alcohol;

carboxylic esters, such as, for example, ethyl acetate, benzyl benzoate, butyl acetate, propylene carbonate, ethyl lactate;

aliphatic hydrocarbons, such as paraffins, cyclohexane, methylene chloride, ethylene chloride;

aromatic hydrocarbons, such as xylene, toluene, alkyl naphthalenes, chlorobenzenes;

ketones, such as, for example, acetone and methyl ethyl ketone, methyl isobutyl ketone, cyclohexanone;

natural and synthetic mono- and triglycerides having natural fatty acids, such as cottonseed oil, peanut oil, maize germ oil, olive oil, castor oil, sesame oil;

furthermore, dimethyl sulphoxide, dimethylacetamide, dimethylformamide, N-methylpyrrolidone, dioxane, 2,2-dimethyl-4-oxymethyl-1,3-dioxolane.

The surfactants include:

emulsifiers and wetting agents, such as anionic surfactants, for example alkylsulphonates, alkyl sulphates, arylsulphonates, Na lauryl sulphates, fatty alcohol ether sulphates, mono/dialkyl polyglycol ether orthophoshoric ester monoethanolamine salt, calcium alkylarylsulphonate;

cationic surfactants, for example cetyltrimethylammonium chloride;

ampholytic surfactants, for example di-Na N-lauryl-beta-iminodipropionate or lecithin;

nonionic surfactants, for example polyethoxylated castor oil, polyethoxylated sorbitan monooleate, polyethoxylated sorbitan monostearate, glycerol monostearate, polyoxyethylene stearate, alkylphenol polyglycol ethers, polyethoxylated sorbitan monopalmitate, polyoxyethylene lauryl ether, polyoxyethylene oleyl ether, polyoxyethylene mannitan monolaurate, alkyl polyglycol ether, oleyl polyglycol ether, dodecyl polyglycol ether, ethoxylated nonylphenol, isooctylphenol polyethoxy ethanol.

The preparations may furthermore comprise:
tackifiers, for example carboxymethylcellulose, methylcellulose and other cellulose and starch derivatives, polyacrylates, alginates, gelatin, gum arabic, polyvinylpyrro-lidone, polyvinyl alcohol, copolymers of methyl vinyl ether and maleic anhydride, polyethylene glycols, paraffins, oils, waxes, hydrogenated castor oil, lecithins and synthetic phospholipids.

The preparations may comprise colorants, such as inorganic pigments, for example iron oxide, titanium oxide, Prussian Blue, and organic dyes, such as alizarine, azo and metal phthalocyanine dyes.

The preparations may comprise spreading agents, for example silicone oils of various viscosity, fatty acid esters, such as ethyl stearate, di-n-butyl-adipate, hexyl laurate, di-propylene glycol pelargonate, esters of a branched fatty acid of medium chain length with saturated fatty alcohols of chain length $C_{16}$–$C_{18}$, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate, ethyl lactate, waxy fatty acid esters, dibutyl phthalate, diisopropyl adipate, ester mixtures related to the latter, inter alia;

triglycerides, such as caprylic/capric triglyceride, triglyceride mixtures with plant fatty acids of chain length $C_8$–$C_{12}$ or other specifically selected natural fatty acids, partial glyceride mixtures of saturated or unsaturated, if appropriate also hydroxyl-group-containing, fatty acids, monodiglycerides of the $C_8$–$C_{10}$-fatty acids and others;

fatty alcohols, such as isotridecyl alcohol, 2-octyldodecanol, cetylstearyl alcohol, oleyl alcohol.

To prepare solid preparations, the active compound is mixed with suitable carriers, if appropriate with addition of auxiliaries, and brought into the desired form.

Carriers which may be mentioned are all physiologically acceptable solid inert substances. These are inorganic and organic substances. Inorganic substances are optionally crushed and fractionated, for example synthetic and natural rock meals, such as kaolins, talc, chalk, quartz, diatomaceous earth, sodium chloride, carbonates, such as calcium carbonate, bicarbonates, aluminium oxides, silicic acids, alumina, precipitated or colloidal silica, phosphates.

Organic substances are, for example, sugar, cellulose, foodstuffs and feeds, such as milk powder, animal meal, grain meals and shreds, starches, sawdust.

Auxiliaries are preservatives, antioxidants, colorants which have already been mentioned above.

Other suitable auxiliaries are lubricants and glidants, such as, for example, magnesium stearate, stearic acid, talc, bentonites, disintegration-promoting substances, such as starch or crosslinked polyvinylpyrrolidone, binders, such as, for example, starch, gelatin or linear polyvinylpyrrolidone, and dry binders, such as microcrystalline cellulose.

The active compounds can be present in their abovementioned solid or liquid formulations, also in encapsulated form.

The active compounds can also be used in the form of an aerosol. To this end, the active compound, in a suitable formulation, is finely distributed under pressure.

It may also be advantageous to use the active compounds in formulations which release the active compound in a delayed manner. Examples which may be mentioned are shaped articles containing the active compound, such as, for example, plates, tapes, strips, collars, ear tags, tail tags, limb bands, halters, marking devices. Other examples are active-compound-containing implants and boluses.

The active compounds can also be administered together with the feed and/or the drinking water.

In its preparations, and in the use forms prepared from these preparations, the active compound according to the invention can be present in a mixture with other active compounds, such as insecticides, sterilants, bactericides, acaricides, nematicides or fungicides. The insecticides include, for example, phosphoric acid esters, carbamates, carboxylic acid esters, chlorinated hydrocarbons, phenylureas, nicotinyls, neonicotinyls, substances produced by microorganisms, etc.

It has furthermore been found that the active compounds according to the invention also have a strong insecticidal action against insects which destroy industrial materials.

The following insects may be mentioned as examples and as preferred—but without a limitation:

Beetles, such as
Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus spec., Tryptodendron spec., Apate monachus, Bostrychus capucins, Heterobostrychus brunneus, Sinoxylon spec., Dinoderus minutus.

Hymenopterons, such as
Sirex juvencus, Urocerus gigas, Urocerus gigas taignus, Urocerus augur.

Termites, such as
Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.

Bristletails, such as Lepisma saccarina.

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising this are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and, if appropriate, dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., turpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, with the proviso that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Suitable additional mixing components are, preferably, the insecticides and fungicides mentioned in WO 94/29 268. The compounds mentioned in this document are an explicit constituent of the present application.

Especially preferred mixing components which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The active compound combinations according to the invention can also be used for protecting against colonization of articles, especially ships' hulls, screens, nets, constructions, quays and signalling equipment, which come into contact with seawater or brackish water.

Colonization by sessile *Oligochaetae,* such as *Serpulidae,* and by shellfish and species of the group Ledamorpha (goose barnacles), such as various *Lepas* and *Scalpellum* species, or by species of the group Balanomorpha (acorn barnacles), such as *Balanus* or *Pollicipes* species, increases the frictional resistance of ships and leads as a result, through increased energy consumption and frequent spells in dry dock, to a marked increase in the operating costs.

In addition to colonization by algae, for example *Ectocarpus* sp. and *Ceramium* sp., particular importance is attached to infestation by sessile Entomostraca groups, which are comprised under the name Cirripedia (*cirriped crustacea*).

Surprisingly, it has now been found that the active compound combinations according to the invention, when used alone or in combination with other active compounds, have a good antifouling (anti-colonization) effect.

By using compounds according to the invention, either alone or combination with other active compounds, it is possible to dispense with the use of heavy metals, such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)-tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, the zinc and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tributyltin halides, or substantially to reduce the concentration of these compounds.

If appropriate, the ready-to-use antifouling paints may comprise yet further active compounds, preferably algicides, fungicides, herbicides, molluscicides or other antifouling active compounds.

Preferred co-components for the antifouling compositions according to the invention are:
algicides, such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides, such as
cyclohexylbenzo[b]thiophenecarboxamide S,S-dioxide, dichlofluanid, fluor-folpet, 3-iodo-2-propinyl butylcarbamate, tolylfluanid and azoles, such as azaconazole, cyproconazole, epoxyconazole, hexaconazole, metconazole, propiconazole and tebuconazole;
molluscicides, such as
fentin acetate, metaldehyde, methiocarb, niclosamid, thiodicarb and trimethacarb;
or customary active antifouling compounds, such as
4,5-dichloro-2-octyl-4-isothiazolin-3-one, diiodomethyl paratryl sulphone, 2-(N,N-dimethylthiocarbamoylthio)-5-nitrothiazyl, potassium, copper, sodium and zinc salts of 2-pyridinethiole 1-oxide, pyridine triphenylborane, tetrabutyldistannoxane, 2,3,-5,6-tetrachloro-4-(methylsulphonyl)-pyridine, 2,4,5,6-tetrachloroisophthalo-nitrile, tetramethylthiuram disulphide and 2,4,6-trichlorophenylmaleimide.

The antifouling compositions used comprise the active compound according to the invention in a concentration of from 0.001 to 50% by weight, in particular from 0.01 to 20% by weight.

The antifouling compositions according to the invention furthermore comprise the customary components as described, for example, in Ungerer, *Chem. Ind.* 1985, 37, 730–732 and Williams, Antifouling Marine Coatings, Noyes, Park Ridge, 1973.

In addition to the algicidal, fungicidal, molluscicidal and insecticidal active compounds according to the invention, antifouling coating compositions comprise, in particular, binders.

Examples of acknowledged binders are polyvinyl chloride in a solvent system, chlorinated rubber in a solvent system, acrylic resins in a solvent system especially in an aqueous system, vinyl chloride/vinyl acetate copolymer systems in the form of aqueous dispersions or in the form of organic solvent systems, buta-diene/styrene/acrylonitrile rubbers, drying oils, such as linseed oil, resin esters or modified hard resins in combination with tar or bitumen, asphalt and also epoxy compounds, small amounts of chlorinated rubber, chlorinated polypropylene and vinyl resins.

Coating compositions also optionally include inorganic pigments, organic pigments or dyestuffs, which are preferably insoluble in salt water. Coating compositions may also comprise materials such as rosin, for a controlled release of the active compounds. The coats may also include plasticizers, modifying agents which influence the rheological properties, and other conventional constituents. The compounds according to the invention or the abovementioned mixtures can also be incorporated into self-polishing antifouling systems.

The active compounds are also suitable for controlling animal pests, in particular insects, arachnids and mites, which are encountered in closed rooms, such as, for example, flats, factory halls, offices, vehicle cabins and the like. They can be used alone or in combination with other active compounds and auxiliaries in household insecticidal products for controlling these pests. They are active against sensitive and resistant species and against all stages of development. These pests include:

From the order of the Scorpionidea, for example, *Buthus occitanus.*

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

From the order of the Araneae, for example, *Aviculariidae, Araneidae.*

From the order of the Opiliones, for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Phthirus pubis.*

From the order of the Heteroptera, for example, *Cimex hemipterus, Cimex lectularius, Rhodinus prolixus, Triatoma infestans.*

In the field of the household insecticides, they are used alone or in combination with other suitable active compounds, such as phosphoric acid esters, carbamates, pyrethroids, growth regulators or active compounds from other known classes of insecticide.

They are used in the form of aerosols, unpressurized sprays, for example pump and atomizer sprays, nebulizers, foggers, foams, gels, vaporizer products with vaporizer tablets made of cellulose or plastic, liquid vaporizers, gel and membrane vaporizers, propeller-operated vaporizers, energyless or passive vaporizer systems, moth papers, moth sachets and moth gels, as granules or dusts, in baits for scattering or bait stations.

The preparation and use of the active compounds according to the invention is shown in the examples below:

PREPARATION EXAMPLES

Example 1

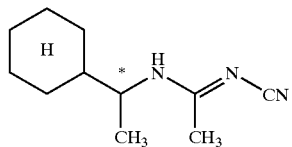

3.3 g (0.03 mol) of methylthio N-cyano-ethane-imidate are added to 3.8 g (0.03 mol) of R-(−)-cyclohexylamine in 30 ml of methanol, and the reaction mixture is stirred at room temperature for 5 hours. The reaction mixture is then concentrated.

This gives 5 g (86% of theory) of R-(−)-N-cyano-N'-cyclohexyl-eth-1-yl-ethane-imid-amide having a log P (pH 2.3) of 2.19.

[The log P values were determined in accordance with EEC directive 79/831 Annex V.A8 by HPLC (gradient method, acetonitrile/0.1% aqueous phosphoric acid)]

The compounds according to the invention of Table 1 are obtained analogously and/or in accordance with the general description of the process:

TABLE 1

$$\underset{H}{R^1-\overset{R^2}{\underset{}{C}}-\overset{R^3}{\underset{}{N}}-C=N-R^4}$$ (I)

| Ex. No. | $R^1$ | $R^2$ | $R^3$ | $R^4$ | log P (pH 2.3) or m.p. (° C.) |
|---|---|---|---|---|---|
| 2 | cyclohexyl | —CH₃ | —OCH₃ | —CN | 2.73 (R isomer) |
| 3 | cyclohexyl | —CH₃ | —SCH₃ | —CN | 2.63 (R isomer) |
| 4 | cyclohexyl | —CH₃ | —NH₂ | NO₂ | 141 (R isomer) |
| 5 | cyclohexyl | —CH₃ | —CH₃ | —CN | 2.20 (S isomer) |
| 6 | cyclohexyl | —CH₃ | —SCH₃ | —CN | 2.74 (S isomer) |
| 7 | cyclohexyl | —CH₃ | —OCH₃ | —CN | 2.73 (S isomer) |
| 8 | cyclohexyl | —CH₃ | —NH₂ | —NO₂ | 139 (S isomer) |
| 9 | cyclohexyl | —C₂H₅ | —CH₃ | —CN | 2.50 (R isomer) |
| 10 | cyclohexyl | —C₂H₅ | —SCH₃ | —CN | 2.94 (R isomer) |
| 11 | cyclohexyl | —C₂H₅ | —NH₂ | —NO₂ | 115 (R isomer) |
| 12 | cyclohexyl | —C₂H₅ | —CH₃ | —CN | 2.51 (S isomer) |
| 13 | cyclohexyl | —C₂H₅ | —SCH₃ | —CN | 2.94 (S isomer) |

(All $R^1$ values shown as cyclohexyl group with H substituent; subscript where applicable)

Note: $R^2$ values in table are written with subscripts: $CH_3$, $C_2H_5$; $R^3$: $OCH_3$, $SCH_3$, $NH_2$, $CH_3$; $R^4$: $CN$, $NO_2$.

TABLE 1-continued $$\underset{R^1}{\overset{R^2}{\diagup}}\underset{\overset{|}{H}}{N}\underset{N}{\overset{R^3}{\diagup}}\diagdown_{R^4} \quad (I)$$

| Ex. No. | R¹ | R² | R³ | R⁴ | log P (pH 2.3) or m.p. (° C.) |
|---|---|---|---|---|---|
| 14 | (cyclohexyl-CH with H) | —C₂H₅ | —NH₂ | —NO₂ | 107 (S isomer) |

Use Examples

Example A
Post-emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of the emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated controls.

In this test, for example, the compound of Preparation Example 7 effects, at an application rate of 2000 g of a.i./ha, a 90% destruction of Abutilon and a 95% destruction of Amaranthus and Sinapis, and is tolerated well by maize.

Example B
Meloidogyne Test

| Solvent: | 4 parts by weight of acetone |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

Containers are filled with sand, solution of active compound, *Meloidogyne incognita* egg/larvae suspension and lettuce seeds. The lettuce seeds germinate and the plants develop. Galls form on the roots.

After 2 weeks, the nematicidal activity is determined by the gall formation in %. 100% means that no galls have been found; 0% activity means that the number of galls on the treated plants corresponds to that of the untreated control.

In this test, for example, the compounds of Preparation Examples 1, 5 and 13 effect a kill of 100%, that of Preparation Example 12 a kill of 99%, that of Preparation Example 10 a kill of 98% and that of Preparation Example 2 a kill of 95%, in each case at an exemplary active compound concentration of 20 ppm.

Example C
*Trichinella spiralis* Larvae Test

*Trichinella spiralis* larvae are isolated from muscles of SPF/CFW1 mice and rinsed repeatedly with a Ringer solution containing Canesten (150 μg/l) and sisomycin (22.6 μg/ml). Per test, about 20 larvae are incubated in 2 ml of solution of the following composition: 20 g/l casitone, 10 g/l yeast extract, 5 g/l glucose, 0.8 g/l potassium dihydrogenphosphate and 0.8 g/l dipotassium hydrogenphosphate pH 7.2. This solution was autoclaved, and sisomycin (15.7 mg/l) and Canesten (100 μg/l) were then added.

The compounds are dissolved in DMSO (concentration 20 mg/ml). The substances are diluted with DMSO. 5 or 10 μl of DMSO solution are then admixed with 2 ml of incubation medium containing the 20 larvae. The mixture is incubated at 37° C. for 3 days. The anthelminthic activity is then determined and evaluated using a scale from 0 to 3: 0=motility corresponds to that of the control, 1=slight motility, 2=good activity, i.e. motility highly effected to rigid, 3=full activity (all larvae dead).

In this test, for example, the compounds of Preparation Examples 2 and 7 show good activity (=2) and the compound of Preparation Example 13 shows full activity (=3), in each case at an exemplary active compound concentration of 100 ppm.

Example D
*Nippostrongylus brasiliensis* (adults) Test

Adult *Nippostrongylus brasiliensis* worms are isolated from the small intestine of female Wistar rats and repeatedly rinsed with a Ringer solution containing 150 μg/l of Canesten and 23.6 μg/ml of sisomycin. As above under Trichinella spiralis, the preparations are taken up in DMSO and prepared. 5 μl of natural compound extract are admixed with 1 ml of incubation medium (see above), and a total of 5 worms (either 3 male and 2 female worms or vice versa) are added. The mixture is then incubated at 37° C. for 4–5 days and the acetylcholinesterase activity in the medium is determined. Evaluation is carried out using a scale from 0 to 3:0 =no activity, 1=weak activity (50–70% reduction of the acetylcholinesterase activity in the medium), 2=good activity (70–90% reduction), 3=full activity (>90% reduction).

In this test, for example, the compounds of Preparation Examples 2 and 7 exhibit good activity (=2) and the compound of Preparation Example 13 exhibits weak activity (=1), in each case at an exemplary active compound concentration of 100 ppm.

What is claimed is:

1. A compound of the formula (I)

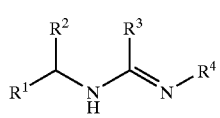

wherein
  R¹ represents optionally substituted cycloalkyl,
  R² represents optionally substituted alkyl or optionally substituted cycloalkyl,
  R³ represents alkyl, alkoxy, alkylthio, amino, alkylamino or dialkylamino and
  R⁴ represents cyano or nitro.

2. A process for preparing the compound of the formula (I) according to claim 1, comprising the step of:
reacting a compound of the formula (II)

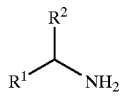

(II)

wherein
$R^1$ and $R^2$ are as defined above with a compound of the formula (III)

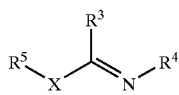

(III)

wherein
$R^3$ and $R^4$ are as defined in claim 1,
$R^5$ represents alkyl and
X represents oxygen or sulphur
in the presence of a diluent.

3. A compound of the formula (I) according to claim 1, wherein
$R^1$ represents $C_3$–$C_8$-cycloalkyl which is optionally mono- to trisubstituted by identical or different substituents selected from the group consisting of halogen, $C_1$–$C_4$-alkyl, $C_1$–$C_4$-alkoxy and $C_1$–$C_4$-alkylthio,
$R^2$ represents $C_1$–$C_4$-alkyl which is optionally substituted by halogen, cyano or $C_1$–$C_4$-alkoxy or represents $C_3$–$C_6$-cycloalkyl which is optionally mono- to trisubstituted by identical or different substituents selected from the group consisting of halogen, $C_1$–$C_4$-alkyl, $C_1$–$C_4$-alkoxy and $C_1$–$C_4$-alkylthio, and
$R^3$ represents $C_1$–$C_4$-alkyl, $C_1$–$C_4$-alkoxy, $C_1$–$C_4$-alkylthio, amino, $C_1$–$C_4$-alkylamino or di-($C_1$–$C_4$)-alkylamino.

4. A compound of the formula (I) according to claim 1, wherein
$R^1$ represents cyclopentyl or cyclohexyl, each of which is optionally mono- to trisubstituted by identical or different substituents selected from the group consisting of fluorine, chlorine, bromine, methyl, ethyl, methoxy, ethoxy, methylthia and ethylthio,
$R^2$ represents methyl, ethyl or n- or i-propyl, each of which is optionally substituted by cyano, fluorine, chlorine, methoxy or ethoxy, or represents cyclopentyl or cyclohexyl, each of which is optionally mono- to trisubstituted by identical or different substituents selected from the group consisting of fluorine, chlorine, bromine, methyl, ethyl, methoxy, ethoxy, methylthio and ethylthio, and
$R^3$ represents methyl, ethyl, n- or i-propyl, n-, i-, s- or t-butyl, methoxy, ethoxy, n- or i-propoxy; methylthio, ethylthio, n- or i-propylthio, amino, methylamino, ethylamino, n- or -propylamino, ethyl-methyl-amino, dimethylamino, diethylamino, methyl-n-propyl-amino, methyl-i-propylamino, ethyl-n-propyl-amino, ethyl-i-propyl-amino, i-propyl-n-propyl-amino or diisopropylamino.

5. A compound of the formula (I) according to claim 1, wherein
$R^1$ represents cyclopentyl or cyclohexyl, each of which is optionally mono- or disubstituted by identical or different substituents selected from the group consisting of chlorine, methyl and methoxy,
$R^2$ represents methyl, ethyl or isopropyl and
$R^3$ represents methyl, ethyl, isopropyl, methoxy, ethoxy, isopropoxy, methylthio, ethylthio, isopropylthio, amino, methylamino, ethylamino, dimethylamino, ethylmethylamino or diethylamino.

6. A pesticide comprising at least one compound of the formula (I) according to claim 1.

7. A method for controlling animal pests and undesirable vegetation, comprising the step of allowing an effective amount of a compound of the formula (I) according to claim 1 to act on said pests, said undesirable plants and/or the habitat of said pests and/or said undesirable plants.

8. A herbicide comprising at least one compound of the formula (I) according to claim 1.

9. A process for preparing a member selected from the group consisting of a pesticide and an herbicide, comprising the step of mixing one or more compounds of the formula (I) according to claim 1 with one or more extenders and/or surfactants.

* * * * *